US010338054B2

(12) United States Patent
Lee et al.

(10) Patent No.: US 10,338,054 B2
(45) Date of Patent: Jul. 2, 2019

(54) METHOD FOR EVALUATING MONOMERS HAVING EFFECT ON COPOLYMER CHARACTERISTICS, AND SYSTEM USING SAME

(71) Applicant: LG Chem, Ltd., Seoul (KR)

(72) Inventors: Seung-Yup Lee, Daejeon (KR); Hye-Won Jeong, Daejeon (KR); Ji-Won Jeong, Daejeon (KR); Kyoung-Hoon Kim, Daejeon (KR)

(73) Assignee: LG Chem, Ltd. (KR)

( * ) Notice: Subject to any disclaimer, the term of this patent is extended or adjusted under 35 U.S.C. 154(b) by 161 days.

(21) Appl. No.: 15/514,125

(22) PCT Filed: Dec. 8, 2015

(86) PCT No.: PCT/KR2015/013408
§ 371 (c)(1),
(2) Date: Mar. 24, 2017

(87) PCT Pub. No.: WO2016/099068
PCT Pub. Date: Jun. 23, 2016

(65) Prior Publication Data
US 2017/0307585 A1    Oct. 26, 2017

(30) Foreign Application Priority Data

Dec. 17, 2014 (KR) ........................ 10-2014-0182226

(51) Int. Cl.
*G01N 33/44* (2006.01)
*G16C 20/30* (2019.01)
*C08G 73/10* (2006.01)

(52) U.S. Cl.
CPC ....... *G01N 33/442* (2013.01); *C08G 73/1042* (2013.01); *C08G 73/1078* (2013.01); *G16C 20/30* (2019.02)

(58) Field of Classification Search
CPC ............................ G01N 33/442; G06F 19/704
See application file for complete search history.

(56) References Cited

U.S. PATENT DOCUMENTS 5,687,090 A    11/1997    Chen et al.

FOREIGN PATENT DOCUMENTS

| EP | 0518406 A1 | 12/1992 |
| JP | 2005082697 A | 3/2005 |
| JP | 2011247630 A | 12/2011 |

OTHER PUBLICATIONS

Darvishi et al., Copolymers of Glycidyl Methacrylate and Octadecyl Acrylate: Synthesis, Characterization, Swelling Properties, and Reactivity Ratios, Jan. 2013, Designed Monomers and Polymers, vol. 16, No. 1, pp. 79-88.*
International Search Report from PCT/KR2015/013408, dated Apr. 19, 2016.
Akbulatov, Sergey, et al., "Force-Reactivity Property of a Single Monomer is Sufficient to Predict the Micromechanical Behavior of Its Polymer." Journal of the American Chemical Society, vol. 134, 2012, pp. 7620-7623.
Lathe, G. H,, et al., "The Separation of Substances and Estimation of their Relative Molecular Sizes by the use of Columns of Starch in Water." Biochem J. 1956, vol. 62, pp. 665-674.

* cited by examiner

*Primary Examiner* — Toan M Le
(74) *Attorney, Agent, or Firm* — Lerner, David, Littenberg, Krumholz & Mentlik, LLP

(57) ABSTRACT

This invention relates to a method of evaluating monomers having an effect on copolymer characteristics and a system using the same, and particularly to a novel method of evaluating the magnitude of the effect of monomers on copolymer characteristics, which cannot be evaluated using existing methods. The method of evaluating monomers having an effect on copolymer characteristics and the system using the same are innovative because the extent of changes in copolymer characteristics can be predicted at the monomer level by quantitatively evaluating the effect of the monomers on the copolymer characteristics, taking into consideration the kind or linkage type of monomers.

18 Claims, No Drawings

METHOD FOR EVALUATING MONOMERS HAVING EFFECT ON COPOLYMER CHARACTERISTICS, AND SYSTEM USING SAME

CROSS-REFERENCE TO RELATED APPLICATIONS

The present application is a national phase entry under 35 U.S.C. § 371 of International Application No. PCT/KR2015/013408, filed Dec. 8, 2015, which claims priority from of Korean Patent Application No. 10-2014-0182226, filed Dec. 17, 2014, all of which are incorporated herein by reference.

TECHNICAL FIELD

The present invention relates to a method of evaluating monomers having an effect on copolymer characteristics and a system using the same, and more particularly to a novel method of evaluating the magnitude of the effect of monomers on copolymer characteristics, which cannot be evaluated using existing methods. The method of evaluating monomers having an effect on copolymer characteristics and the system using the same according to the present invention are innovative because the extent of changes in copolymer characteristics can be predicted at the monomer level by quantitatively evaluating the effect of the monomers on the copolymer characteristics, taking into consideration the kind or linkage type of monomers.

BACKGROUND ART

A copolymer is a material synthesized by linking one or more monomers through a variety of polymerization processes, and is widely utilized in material development and other fields because the properties or characteristics thereof may be controlled at various levels so as to be suitable for respective end uses. One of the factors that greatly affect the characteristics of the synthesized copolymer is the monomers that constitute the copolymer, and the copolymer characteristics vary significantly depending on the number, kind or linkage type of monomers, which are the basic repeating unit of the copolymer. Such changes in copolymer characteristics are determined by the complicated and subtle actions of numerous monomers for the copolymer, but methods of clearly evaluating the effects of monomers on the copolymer characteristics have not yet been devised. Meanwhile, a conventional experimental method (e.g. Gel Permeation Chromatography) is able to measure the properties of a copolymer, such as the molecular weight and viscosity of a copolymer, but is unable to evaluate the effect of the monomers constituting the copolymer on the copolymer characteristics. Therefore, in order to maximize the performance of a copolymer by improving copolymer characteristics and also to design and synthesize copolymers that exhibit new characteristics, there is a need to develop a novel method that is capable of evaluating the effect of monomers on a copolymer.

DISCLOSURE

Technical Problem

Accordingly, the present invention has been made keeping in mind the problems encountered in the related art, and the present invention is intended to provide a novel method of evaluating copolymer characteristics using monomers, suitable for deducing copolymer characteristic factors using monomers, wherein a set of monomer linkages for a copolymer is formed, characteristic displacement values of a copolymer comprising the set of monomer linkages are calculated, and relative characteristic values of the monomers are evaluated based on the calculated characteristic displacement values.

Technical Solution

The present invention provides a method of evaluating monomers having an effect on characteristics of a copolymer comprising two or more monomers, comprising the steps of:

a) selecting monomers $M_k$ for a copolymer and selecting $N_1$ monomers $M_i$ able to form the copolymer together with $M_k$, wherein the $N_1$ monomers $M_i$ are represented as $M_{i1}$, $M_{i2}$, ..., and $M_{iN1}$, $N_1$ is a natural number of 2 or more;

b) calculating $\alpha(M_k)$, $\beta(M_k)$, $\alpha(M_i)$ and $\beta(M_i)$, which are monomer displacement values for the monomers $M_k$ and $M_i$ using Equations 1 to 3 below, $$\alpha(M_i) = A_1 \times \text{Funct}(EC(M_i))/\eta(M_i)$$

$$\beta(M_i) = A_2 \times \text{Funct}(AS(M_i))/\eta(M_i) \quad \text{[Equation 1]}$$

$$\alpha(M_k) = A_1 \times \text{Funct}(EC(M_k))/\eta(M_k)$$

$$\beta(M_k) = A_2 \times \text{Funct}(AS(M_k))/\eta(M_k) \quad \text{[Equation 2]}$$

$$\text{Funct}(x) = a1 * \text{Exp}(a2*x) \text{ or } \text{Funct}(x) = a3 \log(1+a4*x)^{a5} \quad \text{[Equation 3]}$$

in Equations 1 to 3, $A_1$ and $A_2$ are control constants and are real numbers other than zero, $\text{Funct}(x)$ represents a function for the variable x, a1, a2, a3, a4, and a5 are real numbers and are control constants that vary depending on the type of $\text{Funct}(x)$, $\eta(M_i)$ is a value calculated for the monomers $M_i$ and is a Topological Polar Surface Area, a McGowan Volume, an Approximate Surface Area, or an Octanol/Water Partition Coefficient, $EC(M_i)$ represents a Molecular Eccentricity for the monomers $M_i$, and $AS(M_i)$ represents a Molecular Asphericity for the monomers $M_i$; and c) calculating characteristic displacement values $\lambda(M_k; M_i)$ of the monomers $M_i$ relative to the monomers $M_k$ using Equation 4 below and determining the monomer $M_i$ having a relatively high characteristic displacement value to be a monomer having a significant effect on the copolymer characteristics, $$\lambda(M_k; M_i) = \left| 1 - A_3 x \frac{\alpha(M_k)}{\alpha(M_i)} - (1 - A_3) x \frac{\beta(M_k)}{\beta(M_i)} \right| \quad \text{[Equation 4]}$$

in Equation 4, $A_3$ is a control constant and is a real number from 0 to 1.

In addition, the present invention provides a system for evaluating monomers having an effect on characteristics of a copolymer comprising two or more monomers, comprising:

a configuration module for selecting monomers $M_k$ for a copolymer and selecting $N_1$ monomers $M_i$ able to form the copolymer together with $M_k$, wherein the $N_1$ monomers $M_i$ are represented as $M_{i1}$, $M_{i2}$, ..., and $M_{iN1}$, $N_1$ is a natural number of 2 or more;

a calculation module for calculating $\alpha(M_k)$, $\beta(M_k)$, $\alpha(M_i)$ and $\beta(M_i)$, which are monomer displacement values for the monomers $M_k$ and $M_i$ using Equations 1 to 3 below:

$$\alpha(M_i) = A_1 \times \text{Funct}(EC(M_i))/\eta(M_i)$$

$$\beta(M_i) = A_2 \times \text{Funct}(AS(M_i))/\eta(M_i) \quad \text{[Equation 1]}$$

$$\alpha(M_k) = A_1 \times \text{Funct}(EC(M_k))/\eta(M_k)$$

$$\beta(M_k) = A_2 \times \text{Funct}(AS(M_k))/\eta(M_k) \quad \text{[Equation 2]}$$

$$\underset{a5}{\text{Funct}(x) = a1*\text{Exp}(a2*x) \text{ or Funct}(x) = a3 \log(1+a4*x)} \quad \text{[Equation 3]}$$

in Equations 1 to 3, $A_1$ and $A_2$ are control constants and are real numbers other than zero, Funct(x) represents a function for the variable x, a1, a2, a3, a4, and a5 are real numbers and are control constants that vary depending on the type of Funct(x), $\eta(M_i)$ is a value calculated for the monomers $M_i$ and is a Topological Polar Surface Area, a McGowan Volume, an Approximate Surface Area, or an Octanol/Water Partition Coefficient, $EC(M_i)$ represents a Molecular Eccentricity for the monomers M and $AS(M_i)$ represents a Molecular Asphericity for the monomers $M_i$; and an evaluation module for calculating characteristic displacement values $\lambda(M_k;M_i)$ of the monomers $M_i$ relative to the monomers $M_k$ using Equation 4 below and determining the monomer $M_i$ having a relatively high characteristic displacement value to be a monomer having a significant effect on the copolymer characteristics:

$$\lambda(M_k; M_i) = \left| 1 - A_3 x \frac{\alpha(M_k)}{\alpha(M_i)} - (1-A_3)x\frac{\beta(M_k)}{\beta(M_i)} \right| \quad \text{[Equation 4]}$$

in Equation 4, $A_3$ is a control constant and is a real number from 0 to 1.

Advantageous Effects

According to the present invention, the effects of monomers for a copolymer on copolymer characteristics can be similar or significantly different. When there is provided a method of quantitatively clearly evaluating the magnitude of the effect of the monomers on copolymer characteristics, it can be considered to be very useful in material development using copolymers. A method of evaluating copolymer characteristics using monomers according to the present invention is a novel method able to evaluate the magnitude of the effect of the monomers on copolymer characteristics, which cannot be evaluated using existing methods. According to the present invention, the effect of monomers on copolymer characteristics can be quantitatively evaluated taking into consideration the kind and linkage type of monomers, thereby predicting the extent of changes in copolymer characteristics at the monomer level. Furthermore, the present invention enables the copolymer characteristics to be predicted and evaluated using only the monomer characteristics, thus greatly contributing to the selection of optimal monomers for improving the copolymer characteristics and developing novel copolymers having new characteristics.

BEST MODE

Hereinafter, a detailed description will be given of the present invention.

For reference, constants defined in the following Equations of the present invention are values that are determined within a range in which the method of the present invention works well.

The present invention addresses a method of evaluating monomers having an effect on the characteristics of a copolymer comprising two or more monomers, comprising the steps of:

a) selecting monomers $M_k$ for a copolymer and selecting $N_1$ monomers $M_i$ able to form the copolymer together with $M_k$, wherein the $N_1$ monomers $M_i$ are represented as $M_{i1}$, $M_{i2}$, . . . , and $M_{iN1}$, $N_1$ is a natural number of 2 or more;

b) calculating $\alpha(M_k)$, $\beta(M_k)$, $\alpha(M_i)$ and $\beta(M_i)$, which are monomer displacement values for the monomers $M_k$ and $M_i$ using Equations 1 to 3 below, $$\alpha(M_i) = A_1 \times \text{Funct}(EC(M_i))/\eta(M_i)$$

$$\beta(M_i) = A_2 \times \text{Funct}(AS(M_i))/\eta(M_i) \quad \text{[Equation 1]}$$

$$\alpha(M_k) = A_1 \times \text{Funct}(EC(M_k))/\eta(M_k)$$

$$\beta(M_k) = A_2 \times \text{Funct}(AS(M_k))/\eta(M_k) \quad \text{[Equation 2]}$$

$$\underset{a5}{\text{Funct}(x) = a1*\text{Exp}(a2*x) \text{ or Funct}(x) = a3 \log(1+a4*x)} \quad \text{[Equation 3]}$$

in Equations 1 to 3, $A_1$ and $A_2$ are control constants and are real numbers other than zero, Funct(x) represents a function for the variable x, a1, a2, a3, a4, and a5 are real numbers and are control constants that vary depending on the type of Funct(x), $\eta(M_i)$ is a value calculated for the monomers $M_i$ and is a Topological Polar Surface Area, a McGowan Volume, an Approximate Surface Area, or an Octanol/Water Partition Coefficient, $EC(M_i)$ represents a Molecular Eccentricity for the monomers M and $AS(M_i)$ represents a Molecular Asphericity for the monomers M; and c) calculating characteristic displacement values $\lambda(M_k; M_i)$ of the monomers $M_i$ relative to the monomers $M_k$ using Equation 4 below and determining the monomer $M_i$ having a relatively high characteristic displacement value to be a monomer having a significant effect on the copolymer characteristics, $$\lambda(M_k; M_i) = \left| 1 - A_3 x \frac{\alpha(M_k)}{\alpha(M_i)} - (1-A_3)x\frac{\beta(M_k)}{\beta(M_i)} \right| \quad \text{[Equation 4]}$$

in Equation 4, $A_3$ is a control constant and is a real number from 0 to 1, and preferably from 0.3 to 0.8.

Specifically, step a) comprises forming a set of monomer linkages for a copolymer by selecting $N_1$ monomers, the effect on copolymer characteristics of which is to be evaluated, and selecting $N_2$ monomers that may be polymerized into a copolymer through linking with any one monomer of the $N_1$ monomers, in which the number of monomers $M_k$ is $N_2$, and the effects of the $N_1$ monomers $M_i$ on each of the $N_2$ monomers $M_k$ are evaluated. Here, $N_2$ is preferably a natural number of 2 or more.

In the first step a), the copolymer characteristics may include at least one selected from the group consisting of, for example, bonding characteristics, electrical characteristics, and adhesion characteristics, and the $N_1$ monomers, the effect on copolymer characteristics of which is to be evaluated, are selected, and the $N_2$ counterpart monomers, which are polymerizable with the above monomers to give a copolymer, may be selected. According to an embodiment of the present invention, in order to evaluate the effect of monomers on copolymer characteristics, copolymers configured such that monomers (B and C) where $N_1$=2 are linked with a monomer A ($N_2$=1) may be taken into account.

Examples of the linkage type of monomers for forming a copolymer are as follows.

(1) —[—B-A-]$_n$-, a copolymer having a linkage of monomers A and B as a repeating unit (2) —[—C-A-]$_n$-, a copolymer having a linkage of monomers A and C as a repeating unit The magnitude of the effect of monomers on characteristics of the copolymer configured such that the monomer B or monomer C is linked to the monomer A may be evaluated through the calculation in step b).

In the second step b), characteristic values of the copolymer configured to include, as a repeating unit, a linkage of monomers selected from among $N_1*N_2$ monomers in the set of monomer linkages formed in step a) are calculated. Using Equations 1 to 3 for the monomers $M_k$ and $M_i$, the monomer displacement values $\alpha(M_k)$, $\beta(M_k)$, $\alpha(M_i)$ and $\beta(M_i)$ may be calculated.

In Equations 1 and 2 of step b), $A_1$ and $A_2$ are control constants and are real numbers greater than zero. Also, in Equations 1 and 2, $\eta(M_i)$ and $\eta(M_k)$ may be calculated using the ADRIANA.Code program developed by Molecular Network GmbH Computerchemie. Also, in Equations 1 and 2 of step b), $EC(M_i)$, $AS(M_i)$, $EC(M_k)$ and $AS(M_k)$ may be calculated using the ADRIANA.Code program developed by Molecular Network GmbH Computerchemie.

In the third step c), the magnitudes of the characteristic displacement values $\lambda(M_k;M_i)$ of $M_i$ relative to $M_k$ calculated in step b) are compared, and thus the relative characteristic values of the monomers are evaluated. The characteristic displacement values $\lambda(M_k;M_i)$ of the monomers $M_i$ relative to each of the monomers $M_k$ are calculated using Equation 4, and thus a monomer $M_i$ having a relatively high characteristic displacement value may be determined to be a monomer having a significant effect on copolymer characteristics.

The values $\lambda(M_k;M_i)$ calculated in step c) are real numbers greater than zero. The case where $\lambda(M_k;M_i)$ is greater than zero indicates that the effect of the monomer $M_i$ on copolymer characteristics is significant when the copolymer is formed by linking the monomer $M_i$ to the monomer $M_k$. On the other hand, the case where $\lambda(M_k;M_i)$ is so small as to be close to zero indicates that the effect of the monomer $M_i$ on copolymer characteristics is relatively low when the copolymer is formed by linking the monomer $M_i$ to the monomer $M_k$.

In addition, the present invention addresses a system for evaluating monomers having an effect on copolymer characteristics using the aforementioned method of evaluating monomers having an effect on copolymer characteristics.

The system for evaluating monomers having an effect on characteristics of a copolymer comprising two or more monomers includes:

a configuration module for selecting monomers $M_k$ for a copolymer and selecting $N_1$ monomers $M_i$ able to form the copolymer together with $M_k$, wherein the $N_1$ monomers $M_i$ are represented as $M_{i1}, M_{i2}, \ldots,$ and $M_{iN1}$, $N_1$ is a natural number of 2 or more;

a calculation module for calculating $\alpha(M_k)$, $\beta(M_k)$, $\alpha(M_i)$ and $\beta(M_i)$, which are monomer displacement values for the monomers $M_k$ and $M_i$ using Equations 1 to 3 below, $$\alpha(M_i) = A_1 \times \text{Funct}(EC(M_i))/\eta(M_i)$$

$$\beta(M_i) = A_2 \times \text{Funct}(AS(M_i))/\eta(M_i) \quad \text{[Equation 1]}$$

$$\alpha(M_k) = A_1 \times \text{Funct}(EC(M_k))/\eta(M_k)$$

$$\beta(M_k) = A_2 \times \text{Funct}(AS(M_k))/\eta(M_k) \quad \text{[Equation 2]}$$

$$\text{Funct}(x) = a1 * \text{Exp}(a2*x) \text{ or } \text{Funct}(x) = a3 \log(1 + a4*x)$$
$$a5 \quad \text{[Equation 3]}$$

in Equations 1 to 3, $A_1$ and $A_2$ are control constants and are real numbers other than zero, Funct(x) represents a function for the variable x, a1, a2, a3, a4, and a5 are real numbers and are control constants that vary depending on the type of Funct(x), $\eta(M_i)$ is a value calculated for the monomers $M_i$ and is a Topological Polar Surface Area, a McGowan Volume, an Approximate Surface Area, or an Octanol/Water Partition Coefficient, $EC(M_i)$ represents a Molecular Eccentricity for the monomers M and $AS(M_i)$ represents a Molecular Asphericity for the monomers M; and an evaluation module for calculating characteristic displacement values $\lambda(M_k;M_i)$ of the monomers $M_i$ relative to the monomers $M_k$ using Equation 4 below and determining the monomer $M_i$ having a relatively high characteristic displacement value to be a monomer having a significant effect on the copolymer characteristics, $$\lambda(M_k; M_i) = \left| 1 - A_3 x \frac{\alpha(M_k)}{\alpha(M_i)} - (1 - A_3) x \frac{\beta(M_k)}{\beta(M_i)} \right| \quad \text{[Equation 4]}$$

in Equation 4, $A_3$ is a control constant and is a real number from 0 to 1, and preferably from 0.3 to 0.8.

Specifically, in the configuration module as the first module, monomers $M_k$ for a copolymer are selected, and $N_1$ monomers $M_i$ able to form the copolymer together with $M_k$ are selected. Here, the $N_1$ monomers $M_i$ are represented as $M_{i1}, M_{i2}, \ldots,$ and $M_{iN1}$, and the number of monomers $M_k$ is $N_2$ and the effects of the $N_1$ monomers $M_i$ on each of the $N_2$ monomers $M_k$ are evaluated.

In this case, copolymer characteristics may include at least one selected from the group consisting of, for example, bonding characteristics, electrical characteristics, and adhesion characteristics, the $N_1$ monomers, the effect on copolymer characteristics of which is to be evaluated, are selected, and the $N_2$ counterpart monomers, which are polymerizable with the above monomers to give a copolymer, may be designated. According to an embodiment of the present invention, in order to evaluate the effect of monomers on copolymer characteristics, copolymers configured such that monomers (B and C) where $N_1=2$ are linked with a monomer A ($N_2=1$) may be taken into consideration.

Examples of the linkage type of monomers for forming a copolymer are as follows.

(1) —[—B-A-]-, a copolymer having a linkage of monomers A and B as a repeating unit (2) —[—C-A-]-, a copolymer having a linkage of monomers A and C as a repeating unit The magnitude of the effect of monomers on characteristics of the copolymer configured such that the monomer B or monomer C is linked to the monomer A may be evaluated through calculation using the calculation module.

In the calculation module as the second module, characteristic values of the copolymer configured to include, as a repeating unit, a linkage of monomers selected from among $N_1*N_2$ monomers in the set of monomer linkages formed in the configuration module are calculated. Using Equations 1 to 3, the monomer displacement values $\alpha(M_k)$, $\beta(M_k)$, $\alpha(M_i)$ and $\beta(M_i)$ for the monomers $M_k$ and $M_i$ may be calculated.

In Equations 1 and 2 of the calculation module, $A_1$ and $A_2$ are control constants and are real numbers greater than zero. Also, in Equations 1 and 2, $\eta(M_i)$ and $\eta(M_k)$ may be calculated using the ADRIANA.Code program developed by Molecular Network GmbH Computerchemie. Also, in Equations 1 and 2 of the calculation module, $EC(M_i)$, $AS(M_i)$, $EC(M_k)$ and $AS(M_k)$ may be calculated using the ADRIANA.Code program developed by Molecular Network GmbH Computerchemie.

In the evaluation module as the third module, the magnitudes of the characteristic displacement values $\lambda(M_k;M_i)$ of $M_i$ relative to $M_k$, calculated in the calculation module, are compared, and thus the relative characteristic values of the monomers are evaluated. The characteristic displacement values $\lambda(M_k;M_i)$ of the monomers $M_i$ relative to each of the monomers $M_k$ are calculated using Equation 4, and the monomer $M_i$ having a relatively high characteristic displacement value may be determined to be a monomer having a significant effect on copolymer characteristics.

The values $\lambda(M_k;M_i)$ calculated in the evaluation module are real numbers greater than zero. The case where $\lambda(M_k;M_i)$ is greater than zero indicates that the effect of the monomer $M_i$ on copolymer characteristics is significant when the copolymer is formed by linking the monomer $M_i$ to the monomer $M_k$. On the other hand, the case where $\lambda(M_k;M_i)$ is so small as to be close to zero indicates that the effect of the monomer $M_i$ on copolymer characteristics is relatively low when the copolymer is formed by linking the monomer $M_i$ to the monomer $M_k$.

As used herein, the term "module" refers to a unit that is responsible for a specific function or operation, and may be embodied by hardware and software, either alone or in combination.

Mode for Invention

A better understanding of the present invention may be obtained via the following examples, which are set forth to illustrate, but are not to be construed as limiting the scope of the present invention. The scope of the present invention is given by the claims, and also contains all modifications within the meaning and range equivalent to the claims.

Example

Step 1. Configuration of Set of Monomer Linkages for Forming Copolymer

Monomers, $M_{i1}$ and $M_{i2}$, the effects on copolymer characteristics of which are to be evaluated, are 4,4'-diaminodiphenylmethane (CAS Number: 101-77-9) and 3,3'-diaminobenzophenone (CAS Number: 611-79-0), and a monomer $M_k$, which is used to form a copolymer with each of the above two ($N_1$) monomers, is 1,2,4,5-cyclohexane tetracarboxylic dianhydride (CAS Number: 2754-41-8) ($N_2$=1). The copolymer resulting from the linkage of these monomers is polyimide.

[Chemical Formula 1]

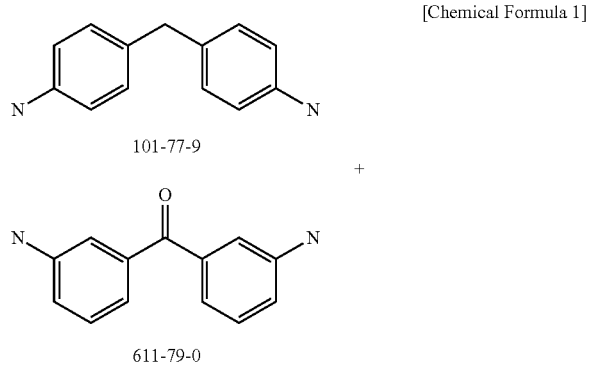

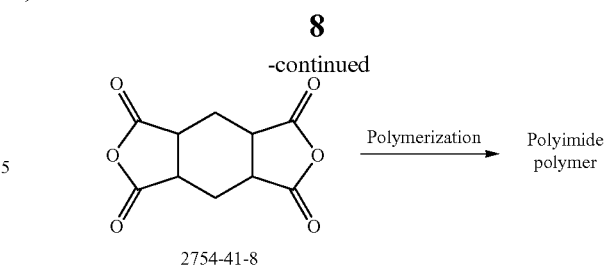

CAS Numbers represented in parentheses of the material names are unique numbers assigned to individual materials, that is, CAS Registry Numbers.

Step 2. Calculation of Characteristic Values of Monomers

Relative characteristic displacement values $\lambda(M_k;M_i)$ of the monomers were calculated using two Funct(X) forms by the following [Equation 1], [Equation 2] and [Equation 4]. The constants used are shown in Tables 1 and 2 below. Funct(x) in Table 1 is Funct(x)=a1*Exp(a2*x), a1=1.0, a2=2.5. Funct(x) in Table 2 is Funct(x)=a3*log(1+a4*x)$^{a5}$, a3=1.0, a4=0.5, a5=2.0.

$$\alpha(M_i) = A_1 \times \text{Funct}(EC(M_i))/\eta(M_i)$$

$$\beta(M_i) = A_2 \times \text{Funct}(AS(M_i))/\eta(M_i) \qquad \text{[Equation 1]}$$

$$\alpha(M_k) = A_1 \times \text{Funct}(EC(M_k))/\eta(M_k)$$

$$\beta(M_k) = A_2 \times \text{Funct}(AS(M_k))/\eta(M_k) \qquad \text{[Equation 2]}$$

$$\lambda(M_k; M_i) = \left| 1 - A_3 x \frac{\alpha(M_k)}{\alpha(M_i)} - (1 - A_3) x \frac{\beta(M_k)}{\beta(M_i)} \right| \qquad \text{[Equation 4]}$$

TABLE 1

| | | | CASE01 | |
|---|---|---|---|---|
| $A_1$ | Funct(x) | $A_2$ | $\eta(M_i)$ | $A_3$ |
| 1.0 | 10*Exp(2.5*x) | 1.0 | Topological Polar Surface Area for monomer $M_i$ | 0.34 |

TABLE 2

| | | | CASE02 | |
|---|---|---|---|---|
| $A_1$ | Funct(x) | $A_2$ | $\eta(M_i)$ | $A_3$ |
| 1.0 | 10*log(1 + 0.5*x)$^2$ | 1.0 | Topological Polar Surface Area for monomer $M_i$ | 0.34 |

$\eta(M_i)$, $EC(M_i)$, and $AS(M_i)$ were calculated using the ADRIANA.Code program made by Molecular Network GmbH Computerchemie. In this case, respective values of $EC(M_{i1})$, $EC(M_{i2})$, $AS(M_{i1})$, $AS(M_{i2})$, $EC(M_k)$, $AS(M_k)$, $\eta(M_{i2})$, $\eta(M_{i2})$ and $\eta(M_k)$ were 0.981, 0.953, 0.318, 0.227, 0.956, 0.233, 69.11, 52.05, and 86.74.

Step 3. Evaluation of Relative Characteristic Values of Monomers

The relative characteristic values of the monomers finally calculated in step 2 are shown in Table 3 below.

TABLE 3

| $M_k$; $M_i$ linkage | $\lambda(M_k; M_i)$ [CASE01] | $\lambda(M_k; M_i)$ [CASE02] |
|---|---|---|
| $M_k$: 1,2,4,5-cyclohexane tetracarboxylic dianhydride<br>$M_i$: 4,4'-diaminodiphenylmethane | 0.4885 | 0.5832 |
| $M_k$: 1,2,4,5-cyclohexane tetracarboxylic dianhydride<br>$M_i$: 3,3'-diaminobenzophenone | 0.1931 | 0.1740 |

As is apparent from the results of Table 3, when a monomer combination with 1,2,4,5-cyclohexane tetracarboxylic dianhydride ($M_k$) is formed to prepare a copolymer, the monomer $M_i$ having a greater effect on copolymer characteristics can be found to be 4,4'-diaminodiphenylmethane (CASE01: 0.4885/CASE02: 0.5832) having a relatively high $\lambda(M_k;M_i)$ value.

In this way, when the magnitudes of $\lambda(M_k;M_i)$ values are compared by evaluating the copolymer characteristics using the monomers, the monomer having a greater effect on copolymer characteristics can be identified. Therefore, the method of the invention is capable of evaluating the magnitude of the effect of monomers on copolymer characteristics, which cannot be evaluated using existing methods, and enables the quantitative evaluation of the effect of monomers on copolymer characteristics in consideration of the kind and linkage type of monomers, whereby the extent of changes in the copolymer characteristics can be accurately predicted at the monomer level.

The invention claimed is:

1. A method of forming a copolymer from two or more monomers having an effect on characteristics of the copolymer comprising:

a) selecting monomers $M_k$ for the copolymer and selecting $N_1$ monomers $M_i$ able to form the copolymer together with the $M_k$, wherein the $N_1$ monomers $M_i$ are represented as $M_{i1}$, $M_{i2}$, . . . , and $M_{iN1}$, $N_1$ is a natural number of 2 or more;

b) calculating $\alpha(M_k)$, $\beta(M_k)$, $\alpha(M_i)$ and $\beta(M_i)$, which are monomer displacement values for the monomers $M_k$ and $M_i$ using Equations 1 to 3 below, $$\alpha(M_i) = A_1 \times \text{Funct}(EC(M_i))/\eta(M_i)$$

$$\beta(M_i) = A_2 \times \text{Funct}(AS(M_i))/\eta(M_i) \quad \text{[Equation 1]}$$

$$\alpha(M_k) = A_1 \times \text{Funct}(EC(M_k))/\eta(M_k)$$

$$\beta(M_k) = A_2 \times \text{Funct}(AS(M_k))/\eta(M_k) \quad \text{[Equation 2]}$$

$$\text{Funct}(x) = a1^*\text{Exp}(a2^*x) \text{ or } \text{Funct}(x) = a3\,\log(1+a4^*x)^{a5} \quad \text{[Equation 3]}$$

wherein in Equations 1 to 3, $A_1$ and $A_2$ are control constants and are real numbers other than zero, Funct(x) represents a function for a variable x, a1, a2, a3, a4, and a5 are real numbers and are control constants that vary depending on a type of Funct(x), $\eta(M_i)$ is a value calculated for the monomers $M_i$ and is a Topological Polar Surface Area, a McGowan Volume, an Approximate Surface Area, or an Octanol/Water Partition Coefficient, $EC(M_i)$ represents a Molecular Eccentricity for the monomers $M_i$, and $AS(M_i)$ represents a Molecular Asphericity for the monomers $M_i$; and c) calculating characteristic displacement values $\lambda(M_k;M_i)$ of the monomers $M_i$ relative to the monomers $M_k$ using Equation 4 below and determining a selected monomer $M_i$ having a relatively high characteristic displacement value to be a monomer having a significant effect on the copolymer characteristics, $$\lambda(M_k;M_i) = \left|1 - A_3 x \frac{\alpha(M_k)}{\alpha(M_i)} - (1-A_3)x\frac{\beta(M_k)}{\beta(M_i)}\right| \quad \text{[Equation 4]}$$

wherein in Equation 4, $A_3$ is a control constant and is a real number from 0 to 1, and forming the copolymer from the selected monomers $M_k$ and $M_i$.

2. The method of claim 1, wherein the number of monomers $M_k$ is $N_2$, $N_2$ is an integer of 2 or more, and effects of the $N_1$ monomers $M_i$ on each of the $N_2$ monomers $M_k$ are evaluated.

3. The method of claim 1, wherein the copolymer characteristics include at least one selected from the group consisting of bonding characteristics, electrical characteristics, and adhesion characteristics.

4. The method of claim 1, wherein, in Equations 1 and 2 of step b), $A_1$ and $A_2$ are control constants and are real numbers greater than zero.

5. The method of claim 1, wherein, in Equations 1 and 2 of step b), $\eta(M_i)$ and $\eta(M_k)$ are calculated using an ADRIANA Code program.

6. The method of claim 1, wherein, in Equations 1 and 2 of step b), $EC(M_i)$, $AS(M_i)$, $EC(M_k)$ and $AS(M_k)$ are calculated using an ADRIANA Code program.

7. The method of claim 1, wherein, in Equation 4 of step c), $A_3$ is a real number from 0.3 to 0.8.

8. The method of claim 1, wherein the values $\lambda(M_k;M_i)$ calculated in step c) are real numbers greater than zero.

9. The method of claim 8, wherein, when the $\lambda(M_k;M_i)$ calculated in step c) is greater than zero, an effect of the monomer $M_i$ on copolymer characteristics is high upon forming the copolymer by linking the monomer $M_i$ to the monomer $M_k$, and when the $\lambda(M_k;M_i)$ is so small as to be close to zero, the effect of the monomer $M_i$ on copolymer characteristics is low upon forming the copolymer by linking the monomer $M_i$ to the monomer $M_k$.

10. A system for preparing a copolymer from two or more monomers having an effect on characteristics of the copolymer comprising:

a configuration module for selecting monomers $M_k$ for the copolymer and selecting $N_1$ monomers $M_i$ able to form the copolymer together with the $M_k$, wherein the $N_1$ monomers $M_i$ are represented as $M_{i1}$, $M_{i2}$, . . . , and $M_{iN1}$, $N_1$ is a natural number of 2 or more;

a calculation module for calculating $\alpha(M_k)$, $\beta(M_k)$, $\alpha(M_i)$ and $\beta(M_i)$, which are monomer displacement values for the monomers $M_k$ and $M_i$ using Equations 1 to 3 below, $$\alpha(M_i) = A_1 \times \text{Funct}(EC(M_i))/\eta(M_i)$$

$$\beta(M_i) = A_2 \times \text{Funct}(AS(M_i))/\eta(M_i) \quad \text{[Equation 1]}$$

$$\alpha(M_k) = A_1 \times \text{Funct}(EC(M_k))/\eta(M_k)$$

$$\beta(M_k) = A_2 \times \text{Funct}(AS(M_k))/\eta(M_k) \quad \text{[Equation 2]}$$

$$\text{Funct}(x) = a1^*\text{Exp}(a2^*x) \text{ or } \text{Funct}(x) = a3\,\log(1+a4^*x)^{a5} \quad \text{[Equation 3]}$$

wherein in Equations 1 to 3, $A_1$ and $A_2$ are control constants and are real numbers other than zero, Funct(x) represents a function for a variable x, a1, a2, a3, a4, and a5 are real numbers and are control constants that vary depending on a type of Funct(x), $\eta(M_i)$ is a value calculated for the monomers $M_i$ and is a Topological Polar Surface Area, a McGowan Volume, an Approximate Surface Area, or an Octanol/Water Partition Coefficient, $EC(M_i)$ represents a Molecular Eccentricity for the monomers $M_i$, and $AS(M_i)$ represents a Molecular Asphericity for the monomers $M_i$; and an evaluation module for calculating characteristic displacement values $\lambda(M_k;M_i)$ of the monomers $M_i$ relative to the monomers $M_k$ using Equation 4 below and determining a selected monomer $M_i$ having a relatively high characteristic displacement value to be a monomer having a significant effect on copolymer characteristics, $$\lambda(M_k; M_i) = \left| 1 - A_3 x \frac{\alpha(M_k)}{\alpha(M_i)} - (1 - A_3) x \frac{\beta(M_k)}{\beta(M_i)} \right| \quad \text{[Equation 4]}$$

wherein in Equation 4, $A_3$ is a control constant and is a real number from 0 to 1, wherein the copolymer can be formed from the selected monomers $M_k$ and $M_i$.

11. The system of claim 10, wherein the number of monomers $M_k$ is $N_2$, $N_2$ is an integer of 2 or more, and effects of the $N_1$ monomers $M_i$ on each of the $N_2$ monomers $M_k$ are evaluated.

12. The system of claim 10, wherein the copolymer characteristics include at least one selected from the group consisting of bonding characteristics, electrical characteristics, and adhesion characteristics.

13. The system of claim 10, wherein, in Equations 1 and 2 of the calculation module, $A_1$ and $A_2$ are control constants and are real numbers greater than zero.

14. The system of claim 10, wherein, in Equations 1 and 2 of the calculation module, $\eta(M_i)$ and $\eta(M_k)$ are calculated using an ADRIANA Code program.

15. The system of claim 10, wherein, in Equations 1 and 2 of the calculation module, $EC(M_i)$, $AS(M_i)$, $EC(M_k)$ and $AS(M_k)$ are calculated using an ADRIANA Code program.

16. The system of claim 10, wherein, in Equation 4 of the evaluation module, $A_3$ is a real number from 0.3 to 0.8.

17. The system of claim 10, wherein the values $\lambda(M_k;M_i)$ calculated in the evaluation module are real numbers greater than zero.

18. The system of claim 17, wherein, when the $\lambda(M_k;M_i)$ calculated in the evaluation module is greater than zero, an effect of the monomer $M_i$ on copolymer characteristics is high upon forming the copolymer by linking the monomer $M_i$ to the monomer $M_k$, and when the $\lambda(M_k;M_i)$ is so small as to be close to zero, the effect of the monomer $M_i$ on copolymer characteristics is low upon forming the copolymer by linking the monomer $M_i$ to the monomer $M_k$.

* * * * *